(12) United States Patent
Rui et al.

(10) Patent No.: US 9,764,317 B2
(45) Date of Patent: Sep. 19, 2017

(54) CATALYSTS FOR PREPARATION OF BUTADIENE BY OXYDEHYDROGENATION OF BUTENE IN FLUIDIZED BED REACTOR AND METHOD OF PREPARING SAME AND USE OF SAME

(71) Applicant: Shanghai Bi Ke Clean Energy Technology Co., Ltd., Shanghai (CN)

(72) Inventors: Guo Rui, Shanghai (CN); Yongsheng Gan, Shanghai (CN); Simon Zhang, Shanghai (CN); Yanning Luo, Shanghai (CN)

(73) Assignee: SHANGHAI BI KE CLEAN ENERGY TECHNOLOGY CO., LTD., Shanghai (CN)

( * ) Notice: Subject to any disclaimer, the term of this patent is extended or adjusted under 35 U.S.C. 154(b) by 136 days.

(21) Appl. No.: 14/414,085

(22) PCT Filed: Jul. 11, 2013

(86) PCT No.: PCT/CN2013/079212
§ 371 (c)(1),
(2) Date: Jan. 9, 2015

(87) PCT Pub. No.: WO2014/008865
PCT Pub. Date: Jan. 16, 2014

(65) Prior Publication Data
US 2015/0165432 A1    Jun. 18, 2015

(30) Foreign Application Priority Data

Jul. 12, 2012    (CN) .......................... 2012 1 0241468

(51) Int. Cl.
*B01J 35/08*    (2006.01)
*B01J 23/78*    (2006.01)
(Continued)

(52) U.S. Cl.
CPC ............. *B01J 35/08* (2013.01); *B01J 23/002* (2013.01); *B01J 23/78* (2013.01); *B01J 23/80* (2013.01);
(Continued)

(58) Field of Classification Search
CPC ... B01J 35/08; B01J 37/06; B01J 37/08; B01J 37/0009; B01J 37/0045; B01J 37/0018;
(Continued)

(56) References Cited

U.S. PATENT DOCUMENTS 3,414,631 A * 12/1968 Grasselli ................ B01J 27/192
585/622
3,595,810 A * 7/1971 Kehl ...................... B01J 23/862
423/594.1
(Continued)

FOREIGN PATENT DOCUMENTS

| CN | 1033013 | * | 5/1989 | ............. B01J 23/76 |
| CN | 1033013 A | | 5/1989 | |

(Continued)

OTHER PUBLICATIONS

International Search Report from PCT Application No. PCT/CN2013/079212 entitled Catalysts for Preparation of Butadiene by Oxydehydrogenation of Butene in Fluidized Bed Reactor and Method of Preparing Same and Use of Same (Dated Sep. 19, 2013).

(Continued)

*Primary Examiner* — Patricia L Hailey
(74) *Attorney, Agent, or Firm* — Hovey Williams LLP

(57) ABSTRACT

The invention relates to a catalyst for preparation of butadiene by oxydehydrogenation of butene in a fluidized bed reactor, a method of preparing the same, and use of the same, wherein a method according to an embodiment of the invention comprises: reacting a metal precursor with an alkaline substance to obtain a slurry containing insoluble (Continued)

compound, followed by filtering and washing the slurry; adding a binder and deionized water, followed by agitation to regulate the solid content of the slurry to 10-50%; subjecting the slurry to spray drying granulation, wherein the temperature at the feed port is controlled between 200-400° C., and the temperature at the discharge port is controlled between 100-160° C., to obtain catalyst microspheres; and drying the catalyst microspheres at 80-200° C. for 1-24 h, and then calcining the catalyst microspheres at 500-900° C. for 4-24 h to obtain a catalyst having a general formula of FeXaYbZcOd, comprising Fe, Mg, Zn, Bi, Mo, Mn, Ni, Co, Ba, Ca, and other metals. The catalyst microspheres prepared according to the exemplary method exhibit high mobility, desirable particle size distribution, extremely high mechanical strength and catalytic activity, and are applicable to industrial production of butadiene by oxydehydrogenation of butene in a fluidized bed. When this catalyst is used to prepare butadiene by oxydehydrogenation of butene, the yield of butadiene is 76-86%, and the selectivity to butadiene is 94-97%.

18 Claims, 1 Drawing Sheet

(51) Int. Cl.
| | |
|---|---|
| B01J 23/80 | (2006.01) |
| B01J 23/83 | (2006.01) |
| C07C 5/48 | (2006.01) |
| B01J 23/847 | (2006.01) |
| B01J 23/889 | (2006.01) |
| B01J 23/00 | (2006.01) |
| B01J 23/843 | (2006.01) |
| B01J 23/86 | (2006.01) |
| B01J 37/00 | (2006.01) |
| B01J 37/08 | (2006.01) |
| B01J 37/12 | (2006.01) |
| B01J 37/03 | (2006.01) |
| B01J 37/06 | (2006.01) |

(52) U.S. Cl.
CPC ........... *B01J 23/83* (2013.01); *B01J 23/8437* (2013.01); *B01J 23/8472* (2013.01); *B01J 23/862* (2013.01); *B01J 23/868* (2013.01); *B01J 23/8892* (2013.01); *B01J 23/8898* (2013.01); *B01J 37/0009* (2013.01); *B01J 37/0018* (2013.01); *B01J 37/0045* (2013.01); *B01J 37/0063* (2013.01); *B01J 37/031* (2013.01); *B01J 37/06* (2013.01); *B01J 37/08* (2013.01); *B01J 37/12* (2013.01); *C07C 5/48* (2013.01); *B01J 2523/00* (2013.01); *C07C 2521/10* (2013.01); *C07C 2523/02* (2013.01); *C07C 2523/06* (2013.01); *C07C 2523/18* (2013.01); *C07C 2523/28* (2013.01); *C07C 2523/34* (2013.01); *C07C 2523/745* (2013.01); *C07C 2523/75* (2013.01); *C07C 2523/755* (2013.01); *C07C 2523/78* (2013.01); *C07C 2523/80* (2013.01); *C07C 2523/83* (2013.01); *C07C 2523/843* (2013.01); *C07C 2523/847* (2013.01); *C07C 2523/86* (2013.01); *C07C 2523/889* (2013.01)

(58) Field of Classification Search
CPC ...... B01J 37/031; B01J 37/12; B01J 37/0063; B01J 23/868; B01J 23/8472; B01J 23/8898; B01J 23/8892; B01J 23/002; B01J 23/862; B01J 23/8437; B01J 23/80; B01J 23/78; B01J 23/83; B01J 21/005; B01J 23/005; C07C 2523/83; C07C 2523/847; C07C 2523/86; C07C 2523/889; C07C 2523/80; C07C 2523/02; C07C 2523/06; C07C 2523/18; C07C 2523/34; C07C 2523/75
USPC ....... 502/302, 305–307, 310, 312, 315, 316, 502/318, 319, 321, 324, 329–331, 343, 502/345, 352, 524, 525
See application file for complete search history.

(56) References Cited

U.S. PATENT DOCUMENTS

| | | | | |
|---|---|---|---|---|
| 3,644,549 | A * | 2/1972 | Innes | B01J 23/868 |
| | | | | 585/442 |
| 3,716,496 | A * | 2/1973 | Yoshino | B01J 23/84 |
| | | | | 502/215 |
| 3,843,745 | A * | 10/1974 | Christman | B01J 23/745 |
| | | | | 502/306 |
| 3,911,039 | A | 10/1975 | Grasselli et al. | |
| 4,220,560 | A * | 9/1980 | Anquetil | B01J 23/86 |
| | | | | 502/306 |
| 4,290,922 | A * | 9/1981 | Umemura | B01J 23/8876 |
| | | | | 502/243 |
| 4,973,793 | A | 11/1990 | McFarland | |
| 8,003,840 | B2 | 8/2011 | Oh et al. | |
| 9,399,606 | B2 * | 7/2016 | Ruttinger | C07C 5/48 |
| 2009/0062108 | A1 | 3/2009 | Demirel et al. | |
| 2013/0217568 | A1* | 8/2013 | Hazin | B01J 27/138 |
| | | | | 502/226 |
| 2014/0141965 | A1* | 5/2014 | Xiong | B01J 27/187 |
| | | | | 502/213 |

FOREIGN PATENT DOCUMENTS

| | | | | |
|---|---|---|---|---|
| CN | 1184705 | A | 6/1998 | |
| CN | 101674883 | * | 3/2010 | ............ B01J 23/80 |
| CN | 101757930 | A | 6/2010 | |
| CN | 102391062 | A | 3/2012 | |
| CN | 102716754 | * | 10/2012 | ............ B01J 23/78 |
| CN | 102716754 | A | 10/2012 | |
| EP | 2177266 | A2 | 4/2010 | |
| WO | 0218043 | A1 | 3/2002 | |
| WO | 2010141379 | A2 | 12/2010 | |

OTHER PUBLICATIONS

Search Report from Chinese Patent Application No. 2012102414680 entitled Catalysts for Preparation of Butadiene by Oxydehydrogenation of Butene in Fluidized Bed Reactor and Method of Preparing Same and Use of Same (Dated Aug. 21, 2013).
Office Action for Chinese Patent Application No. 2012102414680 entitled Catalysts for Preparation of Butadiene by Oxydehydrogenation of Butene in Fluidized Bed Reactor and Method of Preparing Same and Use of Same (Dated Aug. 21, 2013).
Search Report for European Application No. 13816830.7 entitled Catalysts for Preparation of Butadiene by Oxydehydrogenation of Butene in Fluidized Bed Reactor and Method of Preparing Same and Use of Same (Dated Jan. 10, 2015).
Catalysis Today article entitled "The Synthesis of Attrition Resistant Slurry Phase Iron Fischer-Tropsch Catalysts" by Hein N. Pham et al.; vol. 58, No. 4, pp. 233-240 (May 1, 2000).
Office Action from Singapore Application No. 11201408728U entitled Catalysts for Preparation of Butadiene by Oxydehydrogenation of Butene in Fluidized Bed Reactor and Method of Preparing Same and Use of Same (Dated Aug. 28, 2015).

* cited by examiner

CATALYSTS FOR PREPARATION OF BUTADIENE BY OXYDEHYDROGENATION OF BUTENE IN FLUIDIZED BED REACTOR AND METHOD OF PREPARING SAME AND USE OF SAME

CROSS-REFERENCE TO RELATED APPLICATION

This is a National Phase Application pursuant to 37 C.F.R. §371 of International Application No. PCT/CN2013/079212, filed July 11, 2013, claiming priority from Chinese Application No. CN 201210241468.0, filed July 12, 2012, the entire disclosures of both of which are hereby incorporated by reference herein.

TECHNICAL FIELD

The invention pertains to the technical field of catalysis, and relates to a catalyst for preparation of butadiene by oxydehydrogenation of butene in a fluidized bed reactor, a method of preparing the same, and use of the same.

BACKGROUND ART

The rapid development of the rubber and resin industry leads to an evergrowing demand for butadiene in the market. Notwithstanding 1,3-butadiene obtained from naphtha cracking process accounts for 90% of the total production of butadiene, the shortage of the butadiene required has to be covered by oxydehydrogenation of butene due to the domestic limitation of the naphtha output and the cracking units.

Synthesis of butadiene in an industrial scale may be conducted by dehydrogenation or oxydehydrogenation of butene at present. Direct dehydrogenation of butene is a strong endothermic reaction requiring high temperature and low pressure conditions, which suffers from low yield and difficulty in commercialization. In contrast, oxydehydrogenation of butene produces butadiene and water. It is a strong exothermic reaction, and thus the reaction temperature may be decreased appropriately.

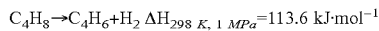

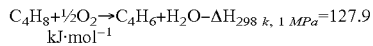

Industrial production of butadiene is carried out by passing a mixed C4 feedstock, steam and air through a fixed or fluidized bed in the presence of a catalyst to produce butadiene. Since the oxydehydrogenation of butene is a strong exothermic reaction, while removal of heat from a fixed bed reactor is difficult, excessive increase of temperature in the catalyst bed is resulted, which is undesirable for temperature control. For a traditional fixed bed reactor used for oxydehydrogenation of butene, a temperature difference of 150-250° C. exists between the teed port and the discharge port, and two reactors, one in preparation and the other in operation, are needed.

In a fluidized bed reactor, the heat produced by oxydehydrogenation of butene can be removed easily, and operation at constant temperature may be realized. Consequently, the catalyst life can be extended, and the catalyst usability can be improved. Moreover, owing to its relatively simple structure, a fluidized bed reactor is easy to manufacture and process, facilitating its industrial scale-up. However, an industrial fixed bed catalyst for oxydehydrogenation of butene cannot be applied to a fluidized reactor for reasons of shape, mechanical strength, wear resistance, etc. It is critically important to synthesize a catalyst which not only is suitable for oxydehydrogenation of butene in a fluidized bed, but also has good wear resistance, high activity, long-term stability in operation, etc.

CN 1184705A and CN1072110A disclose an iron-based catalyst for the preparation of butadiene by oxydehydrogenation of butene. Although this catalyst shows some activity and/or selectivity when used in a baffled fluidized bed, the yield of butadiene is rather low, and severe loss of the catalyst is witnessed, because the catalyst has irregular shape and large particle size. The SEM image of the irregularly shaped catalyst is shown in FIG. 1.

CN101674883 discloses a process for preparing 1,3-butadiene using a zinc ferrite catalyst, wherein a composition comprising zinc ferrite is used, and it's difficult to achieve an ideal catalytic effect. Furthermore, this catalyst is used in a fixed bed reactor. The temperature at the catalyst bed is increased unduly, and the energy consumption is high. Similarly, the wear problem of the catalyst in the fixed bed reactor can not be solved either.

U.S. Pat. No. 8,003,840B2 discloses a process for preparing 1,3-butadiene using a series of bismuth molybdenate catalysts. This series of catalysts are used in a fixed bed reactor, and the problems of wear resistance and high mobility of the catalysts are not solved. Moreover, the catalyst only has moderate catalytic activity.

SUMMARY

The technical problem to be solved by the present invention is to improve the wear resistance and the mobility of a catalyst in a fluidized bed reactor, so as to reduce the loss of the catalyst and enhance the activity, conversion and selectivity of the catalyst.

One object of the invention is to provide a method of preparing a catalyst for preparation of butadiene by oxydehydrogenation of butene in a fluidized bed reactor. As compared with a catalyst prepared using a traditional method, the catalyst prepared by spray drying granulation according to the method provided in this disclosure exhibits higher wear resistance (i.e. mechanical strength) and achieves higher butadiene yield, such that the requirements of a catalyst for synthesizing butadiene in a modern industrial fluidized bed are met. Another object of the invention is to provide method of butene oxydehydrogenation reaction using the catalyst prepared according to the method of the invention to prepare 1,3-butadiene at a high yield.

The invention is fulfilled in a preferred embodiment by the following technical solution:

The method provided in this disclosure comprises the following steps: (1) reacting a metal precursor with an alkaline substance to obtain a slurry containing insoluble compound, followed by filtering and washing the slurry; (2) adding an appropriate amount of a binder and deionized water, followed by sufficient agitation to regulate the solid content of the slurry to 10-50% (mass percentage); (3) subjecting the slurry obtained in step (2) to spray drying granulation in a spray drying granulation device, wherein the temperature at the feed port is controlled between 200-400° C. and the temperature at the discharge port is controlled between 100-160° C. to obtain catalyst microspheres; and (4)drying and then calcining the catalyst microspheres to obtain a catalyst having a general formula FeXaYbZcOd, wherein X is one or more of Ni, Co, Zn, Cu, Sn, Mn, Y is one or more of Bi, Mo, Cr, V, La, Zr, Z is one or more of Mg, Ca, Sr, Ba, a is 0.1-3, b is 0-1, c is 0-1, and the value of d depends on the valence requirement of the other metal elements.

In a preferred embodiment, the reaction between the metal precursor and the alkaline substance is carried out at 10-90° C., preferably 30-80° C., and the pH for this reaction is 5-11, preferably 6-10.

In another preferred embodiment, the slurry in step (1) is filtered and washed to a pH of 7-7.5.

In another preferred embodiment, the catalyst microspheres are dried in step (4) at 80-200° C., preferably 80-180° C. for 1-24 h, preferably 4-16 h.

In another preferred embodiment, the catalyst microspheres are calcined in step (4) at 500-900° C., preferably 520-820° C. for 4-24 h, preferably 4-18 h.

Preferably, the method provided in this disclosure comprises the following steps: (1) reacting a metal precursor with an alkaline substance at 10-90° C. and a pH of 5-11 to obtain a slurry containing insoluble compound, followed by filtering and washing the slurry to a pH of 7-7.5; (2) adding an appropriate amount of a binder and deionized water, followed by sufficient agitation to regulate the solid content of the slurry to 10-50%, preferably 20-45% (mass percentage); (3) subjecting the slurry obtained in step (2) to spray drying granulation in a spray drying granulation device, wherein the temperature at the feed port is controlled between 200-400° C., preferably 220-350° C. and the temperature at the discharge port is controlled between 100-160° C., preferably 110-150° C., to obtain catalyst microspheres having a preferred particle size of 20-600 μm; and (4) drying the catalyst microspheres at 80-200° C. for 1-24 h, and then calcining it at 500-900° C. for 4-24 h to obtain a catalyst having a general formula $FeX_aY_bZ_cO_d$, wherein X is one or more of Ni, Co, Zn, Cu, Sn, Mn, Y is one or more of Bi, Mo, Cr, V, La, Zr, Z is one or more of Mg, Ca, Sr, Ba, a is 0.1-3, b is 0-1, c is 0-1, and the value of d depends on the valence requirement of the other metal elements.

In a preferred embodiment of the inventive method, the metal precursor is selected from a group consisting of nitrates, chlorides, sulfates, hydroxides, oxides, ammonium metallates, and a mixture of two or more of the above substances.

In a preferred embodiment of the inventive method, the alkaline substance is selected from a group consisting of sodium hydroxide, potassium hydroxide, sodium carbonate, sodium dicarbonate, potassium carbonate, potassium dicarbonate, aqueous ammonia, urea, and a mixture of two or more of the above substances.

In a preferred embodiment of the inventive method, the reaction between the metal precursor and the alkaline substance is carried out by adding the metal precursor dropwise to the alkaline substance, or adding the alkaline substance dropwise to the metal precursor, or adding the metal precursor and the alkaline substance dropwise and concurrently, and controlling the final pH to 6-10.

In a preferred embodiment of the inventive method, the metal precursor and the alkaline substance react at 30-80° C.

In a preferred embodiment of the inventive method, the binder is selected from the group consisting of silica gel, alumina gel, methylcellulose, polyvinyl alcohol, sesbania powder, and a mixture of two or more of the above substances; and the binder is added at an amount of 1-5% (mass percentage).

In a preferred embodiment of the inventive method, the solid content of the slurry is 20-45% (mass percentage).

In a preferred embodiment of the inventive method, the spray drying granulation device is a pressure spray drying granulation device, pneumatic spray drying granulation device, or a centrifugal spray drying granulation device.

In a preferred embodiment of the inventive method, the temperature at the feed port is 220-350° C., the temperature at the discharge port is 110-150° C., and microspheres having a particle size of 20-600 μm are obtained.

In a preferred embodiment of the inventive method, the drying is carried out at 80-180° C. for 4-16 h.

In a preferred embodiment of the inventive method, the calculation is carried out at 520-820° C. for 4-18 h.

An embodiment of the invention further provides a method of preparing 1,3-butadiene using the catalyst prepared according to the invention, comprising: carrying out a reaction at 300-400° C., ambient pressure in the presence of the catalyst prepared according to the invention to obtain 1,3-butadiene, wherein the molar ratio of water to butene is 6-16, the molar ratio of oxygen to butene is 0.4-1.0, and the volume space velocity of butene is 100-600 $h^{-1}$.

A catalyst prepared according to embodiments of the invention has the following beneficial effects: (1) owing to the selection of a suitable raw material composition and operational conditions in the preparation of the catalyst, the catalyst has good catalytic performances such as catalytic activity, conversion and selectivity; (2) owing to the selection of spray drying granulation as the shaping process and suitable operational conditions, the resulting catalyst has higher wear resistance and mobility than a catalyst prepared using the traditional methods, and meets the requirements of a fluidized bed reactor for industrial production of butadiene by oxydehydrogenation of butene; and (3) an increased yield of butadiene can be achieved by using this catalyst, and this catalyst has a long service lifetime, low wear and high usability.

DETAILED DESCRIPTION OF THE PREFERRED EMBODIMENTS

Figure 1:
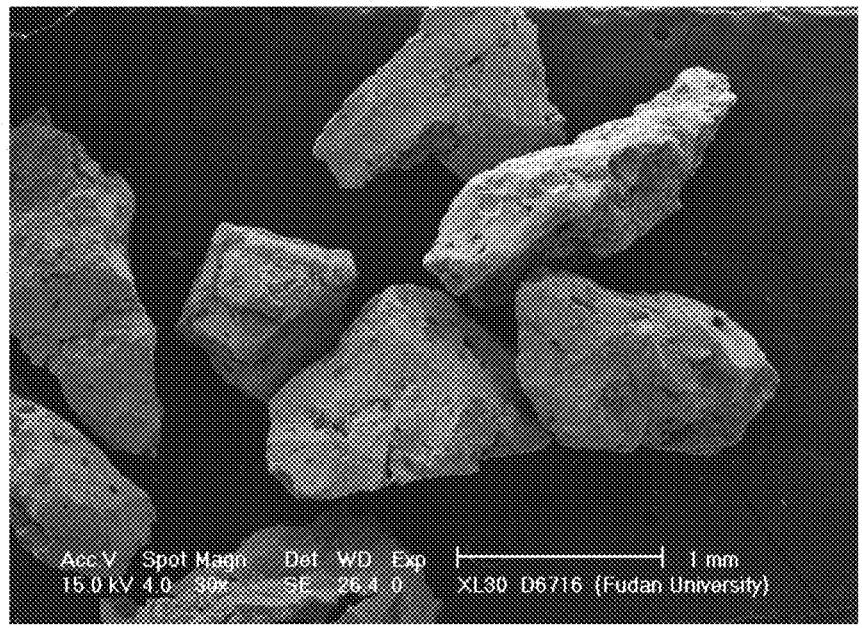
FIG. 1 shows a SEM image of an irregularly shaped catalyst according to the prior art.

The features of exemplary embodiments of the invention will be illustrated in detail with reference to the following examples.

EXAMPLE 1

A mixed solution A of ferric nitrate, manganese nitrate, zinc nitrate and cobalt nitrate was formulated, wherein the concentrations of $Fe^{3+}$, $Mn^{2+}$, $Zn^{2+}$ and $Co^{2+}$ ions were 1 mol/L, 1 mol/L, 1 mol/L and 1 mol/L respectively. A 0.5 mol/L sodium carbonate solution was also formulated. Solution A and the sodium carbonate solution were added cocurrently and dropwise to a reaction kettle under strong agitation, wherein 2000 mL solution A was added dropwise to the reaction kettle, the reaction temperature was controlled at 60° C., and the pH was 8-9. A slurry containing insoluble compound was obtained, and then the slurry was filtered and washed until the pH reached 7-7.5. After washing, 2% methylcellulose and deionized water were added to the above slurry under full agitation, and the solid content was regulated to 20%. The fully agitated slurry was fed to a pressure spray drying granulation device to obtain catalyst microspheres, Wherein the temperature at the feed port was controlled at 280° C. and that the temperature at the discharge port was controlled at 130° C. The microspheres obtained by the spray drying granulation were dried at 120° C. for 14 h, and then calcined at 700° C. for 10 h to obtain a finial catalyst product.

EXAMPLE 2

A mixed solution A of ferric chloride, cupric chloride, cobalt nitrate and barium chloride was formulated, wherein the concentrations of $Fe^{3+}$, $Cu^{2+}$, $Co^{2+}$ and $Ba^{2+}$ ions were 1 mol/L, 1 mol/L, 1 mol/L and 1 mol/L respectively. A 0.37 mol/L potassium hydroxide solution was also formulated. Firstly, 2000 mL solution A was added to a reaction kettle, and then the potassium hydroxide solution was added dropwisely to the reaction kettle under intense agitation. The reaction temperature was controlled at 30° C., and the pH was controlled at 10-11. A slurry containing insoluble compound was obtained, and then the slurry was filtered and washed to a pH of 7-7.5. After washing, 1.8% polyvinyl alcohol having a molecule weight of 6000 and deionized water were added to the above slurry under full agitation, and the solid content was regulated to 35%. The fully agitated slurry was fed to a pneumatic spray drying granulation device to obtain catalyst microspheres, wherein the temperature at the feed port was controlled at 300° C. and that the temperature at the discharge port was controlled at 140° C. The microspheres obtained by spray drying granulation were dried at 80° C. for 23 h, and then calcined at 800° C. for 9 h to obtain a finial catalyst product.

EXAMPLE 3

560 mL of 65% concentrated nitric acid was diluted to 2000 mL by adding distilled water therein, and then iron chips and nickel powder were added slowly. After the iron chips and nickel powder were dissolved completely, magnesia, barium hydroxide and bismuth chloride were added under intense agitation to obtain a mixed solution A, wherein the concentrations of $Fe^{3+}$, $Ni^{2+}$, $Mg^{2+}$, $Ba^{2+}$ and $Bi^{3+}$ ions were 1 mol/L, 1 mol/L, 0.2 mol/L, 0.3 mol/L and 1 mol/L, respectively. A mixed solution B of 0.25 mol/L sodium dicarbonate and 0.25 mol/L sodium hydroxide was also formulated. Firstly, 2000 mL solution B was added to a reaction kettle, and then said solution A was added dropwisely to the reaction kettle under intense agitation. The reaction temperature was controlled at 50° C., and the pH was 5-6. A slurry containing insoluble compound was obtained, and then the slurry was filtered and washed to a pH of 7-7.5. After washing, 5% silica gel and deionized water were added to the above stated slurry under full agitation, and the solid content was regulated to 50%. The fully agitated slurry was fed to a pneumatic spray drying granulation device to obtain catalyst microspheres, wherein the temperature at the feed port was controlled at 350° C. and that the temperature at the discharge port was controlled at 120° C. The microspheres obtained by spray drying granulation were dried at 180° C. for 6 h, and then calcined at 520° C. for 18 h to obtain a finial catalyst product.

EXAMPLE 4

A mixed solution A of ferric nitrate, manganese chloride, tin chloride and calcium chloride was formulated, wherein the concentrations of $Fe^{3+}$, $Mn^{2+}$, $Sn^{4+}$ and $Ca^{2+}$ ions were 1 mol/L, 0.1 mol/L, 0.4 mol/L and 0.6 mol/L, respectively. A 18% aqueous ammonia was also formulated, Solution A and the aqueous ammonia solution were added concurrently and dropwisely to a reaction kettle under intense agitation, wherein 2000 ml, solution A was added dropwise to the reaction kettle, the reaction temperature was controlled at 40° C., and the pH was 9-10. A slurry containing insoluble compound was obtained, and then the slurry was filtered and washed to a pH of 7-7.5. After washing, 1% sesbania powder, 1% alumina gel and deionized water were added to the above stated slurry under full agitation, and the solid content was regulated to 45%. The fully agitated slurry was fed to a centrifugal spray drying granulation device to obtain catalyst microspheres, wherein the temperature at the feed port was controlled at 220° C. and that the temperature at the discharge port was controlled at 100° C. The microspheres obtained by spray drying granulation were dried at 100° C. for 16 h, and then calcined at 900° C. for 4 h to obtain a finial catalyst product.

EXAMPLE 5

A mixed solution A of ferric chloride, zinc nitrate, lanthanum nitrate and barium chloride was formulated, wherein the concentrations of $Fe^{3+}$, $Zn^{2+}$, $La^{3+}$ and $Ba^{2+}$ ions were 1 mol/L, 0.1 mol/L, 0.5 mol/L and 0.3 mol/L, respectively. A 0.4 mol/L potassium carbonate solution was also formulated. Firstly, 2000 mL solution A was added to a reaction kettle, and then the potassium carbonate solution was added dropwisely to the reaction kettle under intense agitation. The reaction temperature was controlled at 90° C., and the pH was 8-9. A slurry containing insoluble compound was obtained, and then the slurry was filtered and washed to a pH of 7-7.5. After washing, 3% methylcellulose and deionized water were added to the above stated slurry under full agitation, and the solid content was regulated to 25%. The fully agitated slurry was fed to a centrifugal spray drying granulation device to obtain catalyst microspheres, wherein the temperature at the feed port was controlled at 400° C. and that the temperature at the discharge port was controlled at 160° C. The microspheres obtained by spray drying granulation were dried at 200° C. for 2 h, and then calcined at 650° C. for 15 h to obtain a finial catalyst product.

EXAMPLE 6

A mixed solution A of ferric nitrate, nickel nitrate, zinc chloride and strontium chloride was formulated, wherein the concentrations of $Fe^{3+}$, $Ni^{2+}$, $Zn^{2+}$ and $Sr^{2+}$ ions were 1 mol/L, 0.8 mol/L, 0.7 mol/L and 0.8 mol/L, respectively. A 0.45 mol/L urea solution was also formulated. Firstly, 2000 mL solution A was added to a reaction kettle, and then the urea solution was added dropwise to the reaction kettle under intense agitation. The reaction temperature was controlled at 80° C., and the pH was 7-8. A slurry containing insoluble compound was obtained, and then the slurry was filtered and washed to a pH of 7-7.5. After washing, 1% methylcellulose and deionized water were added to the above stated slurry under full agitation, and the solid content was regulated to 10%. The fully agitated slurry was fed to a pressure spray drying granulation device to obtain catalyst microspheres, wherein the temperature at the feed port was controlled at 200° C. and temperature at the discharge port was controlled at 150° C. The microspheres obtained by spray drying granulation were dried at 150° C. for 12 h, and then calcined at 500° C. for 23 h to obtain a finial catalyst product.

EXAMPLE 7

A mixed solution A of ferric chloride, manganese nitrate, zirconium nitrate and ammonium dimolybdate was formulated, wherein the concentrations of $Fe^{3+}$, $Mn^{2+}$, $Zr^{4+}$ and $Mo^{6+}$ ions were 1 mol/L, 2.2 mol/L, 0.5 mol/L and 0.3 mol/L respectively. A 0.6 mol/L potassium dicarbonate solution was also formulated. Firstly, 2000 mL of the potassium dicarbonate solution was added to a reaction kettle, and then said solution A was added dropwise to the reaction kettle under intense agitation. The reaction temperature was controlled at 10° C., and the pH was 6-7. A slurry containing insoluble compound was obtained, and then the slurry was filtered and washed to a pH of 7-7.5. After washing, 2% alumina gel and deionized water were added to the above stated slurry under full agitation, and the solid content was regulated to 30%. The fully agitated slurry was fed to a pneumatic spray drying granulation device to obtain catalyst microspheres, wherein the temperature at the feed port was controlled at 230° C. and that the temperature at the discharge port was controlled at 110° C. The microspheres obtained by spray drying granulation were dried at 160° C. for 8 h, and then calcined at 600° C. for 14 h to obtain a finial catalyst product.

EXAMPLE 8

A mixed solution A of ferric chloride, cupric sulfate and chromic chloride was formulated, wherein the concentrations of $Fe^{3+}$, $Cu^{2+}$ and $Cr^{3+}$ ions were 1 mol/L, 1.2 mol/L and 0.61 mol/L, respectively. A 0.5 mol/L sodium hydroxide solution was also formulated. Firstly, 2000 mL of the sodium hydroxide solution was added to a reaction kettle, and then the solution A was added dropwise to the reaction kettle under intense agitation. The reaction temperature was controlled at 50° C., and the pH was 7.5-8. A slurry containing insoluble compound was obtained, and then the slurry was filtered and washed to a pH of 7-7.5. After washing, 2% alumina gel and deionized water were added to the above stated slurry under full agitation, and the solid content was regulated to 40%. The fully agitated slurry was fed to a pneumatic spray drying granulation device to obtain catalyst microspheres, wherein the temperature at the feed port was controlled at 260° C. and the temperature at the discharge port was controlled at 140° C. The microspheres obtained by spray drying granulation were dried at 130° C. for 1.0 h, and then calcined at 750° C. for 10 h to obtain a finial catalyst product.

EXAMPLE 9

A mixed solution A of ferric chloride, zinc chloride and vanadium trichloride was formulated, wherein the concentrations of $Fe^{3+}$, $Zn^{2+}$, $V^{3+}$ ions were 1 mol/L, 0.9 mol/L and 0.7 mol/L, respectively. A 0.65 mol/L potassium dicarbonate solution was also formulated. Firstly, 2000 mL of the potassium dicarbonate solution was added to a reaction kettle, and then solution A was added dropwise to the reaction kettle under intense agitation. The reaction temperature was controlled at 65° C., and pH was 8-8.5. A slurry containing insoluble compound was obtained, and then the slurry was filtered and washed to 7-7.5. After washing, 2.2% sesbania powder and deionized water were added to the above stated slurry under full agitation, and the solid content was regulated to 36%. The fully agitated slurry was fed to a centrifugal spray drying granulation device to obtain catalyst microspheres, wherein the temperature at the feed port was controlled at 320° C. and the temperature at the discharge port was controlled at 120° C. The microspheres obtained by spray drying granulation were dried at 190° C. for 5 h, and then calcined at 820° C. for 8 h to obtain a finial catalyst product.

Figure 2:
FIG. 2 shows a SEM image of a spherical catalyst prepared according to a method of an embodiment of the invention.

The SEM image of the final spherical catalyst product obtained using a method of an embodiment of the invention is shown in FIG. 2. As indicated by comparison between FIG. 1 and FIG. 2, the catalyst prepared according to the method has a spherical shape, good mobility and high wear resistance. The catalyst of the present application is apparently distinguishable from the catalyst of the prior art which has irregular shape.

Test Method for Evaluating Catalysts

The catalysts prepared in Examples 1-9 were compressed into tablet and pulverized, and then particles with a particle size of 20-40 mesh were sieved out and loaded in a 10 mL fixed bed reactor, wherein the volume space velocity of butene was 400 $h^{-1}$, the molar ratio of oxygen to butene was 0.67, the molar ratio of water to butene was 12, the reaction temperature was 340° C., and the reaction was conducted at ambient pressure. The reaction lasted for 6 h, and the contents contained in the reaction system were sampled every 2 h, and the average of the measurement results was taken as the final result. Gas chromatography was used to determine the products. At the same time, comparative tests were conducted under the same conditions using catalyst I and catalyst II which were commercially available and generally used for preparation of butadiene by oxydehydrogenation of butene, and the test results were shown in Table 1 below.

TABLE 1

Test results of the catalysts

| | Butadiene Yield (%) | Butadiene Selectivity (%) |
|---|---|---|
| Example 1 | 83.9 | 94.7 |
| Example 2 | 85.2 | 94.2 |
| Example 3 | 83.1 | 95.2 |
| Example 4 | 80.2 | 96.5 |
| Example 5 | 78.4 | 95.4 |
| Example 6 | 84.2 | 94.5 |
| Example 7 | 84.6 | 95.8 |
| Example 8 | 81.9 | 94.9 |
| Example 9 | 82.3 | 96.7 |
| Catalyst | 75.5 | 94.4 |
| Catalyst | 76.2 | 93.8 |

As indicated by Table 1, as compared with the catalysts of the prior art, the catalysts obtained according to embodiments of the invention afford butadiene with yield and selectivity improved to a certain degree. Particularly, the yield of butadiene is enhanced significantly.

What is claimed is:

1. A method of preparing a catalyst for preparation of butadiene by oxydehydrogenation of butene in a fluidized bed reactor, said method comprising the steps of:
    (1) reacting a metal precursor with an alkaline substance to obtain a slurry containing an insoluble compound, followed by filtering and washing the slurry;
    (2) adding an appropriate amount of a binder and deionized water, followed by agitating to regulate the solid content of the slurry to 10-50%, wherein the percentage is calculated by mass;
    (3) subjecting the slurry obtained in step (2) to spray drying granulation in a spray drying granulation device, wherein the temperature at the feed port is controlled between 200-400° C., and the temperature at the discharge port is controlled between 100-160° C., to obtain catalyst microspheres having a particle size of 20-600µm; and (4) drying and calcining the catalyst microspheres to obtain the catalyst, said catalyst having a general formula of $FeCo_1Zn_1Mn_1O_d$, wherein:
the value of d is based on the valence requirement of the other metal elements.

2. The method as claimed in claim 1, wherein the reaction between the metal precursor and the alkaline substance is carried out at a temperature of 10-90° C. and a pH of 5-11.

3. The method as claimed in claim 1, wherein the slurry in step (1) is filtered and washed to a pH of 7-7.5.

4. The method as claimed in claim 1, wherein the catalyst microspheres are dried in step (4) at a temperature of 80-200° C. for 1-24h.

5. The method as claimed in claim 1, wherein the catalyst microspheres are calcined in step (4) at a temperature of 500-900° C. for 4-24h.

6. The method as claimed in claim 1, wherein the metal precursor is selected from a group consisting of nitrates, chlorides, sulfates, hydroxides, oxides, ammonium metallates, and a mixture of at least two of the above substances.

7. The method as claimed in claim 1, wherein the alkaline substance is selected from a group consisting of sodium hydroxide, potassium hydroxide, sodium carbonate, sodium dicarbonate, potassium carbonate, potassium dicarbonate, ammonia, urea, and a mixture of at least two of the above substances.

8. The method as claimed in claim 1, wherein the reaction between the metal precursor and the alkaline substance is carried out by:
one of (i) adding the metal precursor dropwise to the alkaline substance,(ii) adding the alkaline substance dropwise to the metal precursor, and adding the metal precursor and the alkaline substance dropwise and concurrently, and
controlling the final pH to 6-10.

9. The method as claimed in claim 1, wherein the binder is selected from a group consisting of silica gel, alumina gel, methylcellulose, polyvinyl alcohol, sesbania powder, and a mixture of at least two of the above substances, and is added at an amount of 1-5% by mass.

10. The catalyst prepared according to the method of claim 1.

11. The method as claimed in claim 1, further comprising preparing 1, 3-butadiene using the catalyst, wherein a reaction is carried out at a temperature of 300-400° C. and ambient pressure in the presence of the catalyst to obtain 1,3-butadiene, wherein the molar ratio of water to butene is from 6:1 to 16:1, the molar ratio of oxygen to butene is from 0.4:1 to 1.0:1, and the volume space velocity of butene is 100-600 $h^{-1}$.

12. A method of preparing a catalyst for preparation of butadiene by oxydehydrogenation of butene in a fluidized bed reactor, said method comprising the steps of:

(1) reacting a metal precursor with an alkaline substance at a temperature of 10-90° C. and a pH of 5-11 to obtain a slurry containing an insoluble compound, followed by filtering and washing the slurry to a pH of 7-7.5;

(2) adding an appropriate amount of a binder and deionized water, followed by agitating to regulate the solid content of the slurry to 10-50% wherein the percentage is calculated by mass;

(3) subjecting the slurry obtained in step (2) to spray drying granulation in a spray drying granulation device, wherein the temperature at the feed port is controlled between 200-400° C., and the temperature at the discharge port is controlled between 100-160° C., to obtain catalyst microspheres having a particle size of 20-600µm; and (4) drying the catalyst microspheres at a temperature of 80-200° C. for 1-24h and then calcining the catalyst microspheres at a temperature of 500-900° C. for 4-24h, to obtain the catalyst, said catalyst having a general formula of $FeCo_1Zn_1Mn_1O_d$, wherein:
the value of d is based on the valence requirement of the other metal elements.

13. The method as claimed in claim 12, wherein the metal precursor is selected from a group consisting of nitrates, chlorides, sulfates, hydroxides, oxides, ammonium metallates, and a mixture of at least two of the above substances.

14. The method as claimed in claim 12, wherein the alkaline substance is selected from a group consisting of sodium hydroxide, potassium hydroxide, sodium carbonate, sodium dicarbonate, potassium carbonate, potassium dicarbonate, ammonia, urea, and a mixture of at least two of the above substances.

15. The method as claimed in claim 12, wherein the reaction between the metal precursor and the alkaline substance is carried out by:
one of (i) adding the metal precursor dropwise to the alkaline substance, (ii) adding the alkaline substance dropwise to the metal precursor, and adding the metal precursor and the alkaline substance dropwise and concurrently, and
controlling the final pH to 6-10.

16. The method as claimed in claim 12, wherein the binder is selected from a group consisting of silica gel, alumina gel, methylcellulose, polyvinyl alcohol, sesbania powder, and a mixture of at least two of the above substances, and is added at an amount of 1-5% by mass.

17. The method as claimed in claim 12, further comprising preparing 1, 3-butadiene using the catalyst, wherein a reaction is carried out at a temperature of 300-400° C. and ambient pressure in the presence of the catalyst to obtain 1,3-butadiene, wherein the molar ratio of water to butene is from 6:1 to 16:1, the molar ratio of oxygen to butene is from 0.4:1 to 1.0:1, and the volume space velocity of butene is 100-600 $h^{-1}$.

18. The catalyst prepared according to the method of claim 12.

* * * * *